US00PP08637P

United States Patent [19]

van Diemen

[11] Patent Number: Plant 8,637

[45] Date of Patent: Mar. 8, 1994

[54] *FICUS BENJAMINA* PLANT NAMED MONIQUE

[75] Inventor: Hubertus T. van Diemen, RS Vrouwenakker, Netherlands

[73] Assignee: Kwekerij De Amstel, Vrouwenakker, Netherlands

[21] Appl. No.: 984,092

[22] Filed: Dec. 1, 1992

[51] Int. Cl.[5] ..... A01H 5/00

[52] U.S. Cl. ..... Plt./88.9

[58] Field of Search ..... Plt. 88.9

[56] References Cited

PUBLICATIONS

*The New Royal Horticultural Society Dictionary of Gardening.* Huxley et al., eds., MacMillan Press, London. 1992.

*Primary Examiner*—James R. Feyrer
*Assistant Examiner*—Elizabeth C. Kemmerer
*Attorney, Agent, or Firm*—Christie, Parker & Hale

[57] ABSTRACT

A *Ficus benjamina* plant having hard, rigid ovate leaves which are undulate-crenate in form.

1 Drawing Sheet

BACKGROUND OF THE INVENTION

The present invention comprises a new and distinct cultivar of *Ficus benjamina.* The varietal denomination of the new cultivar is 'Monique'.

The new variety was discovered as a mutation in a controlled planting of *Ficus benjamina* Exotica in a greenhouse in Kwekerij De Amstel, Aalsmeer, The Netherlands.

SUMMARY OF THE INVENTION

The new variety is a mutation of the variety *Ficus benjamina* Exotica and differs significantly in appearance from its parent. The leaves of the new variety are undulate-crenate and darker in color than the parent. In addition, the new variety is more resistant to leaf drop under conditions of stress and is highly pest and disease-resistant. The young leaves of the new variety display a small dark-green spot under low light conditions in the winter months, e.g., about 21° C., 30,000 lux, in the months of November, December and January, over a three-year period. As compared to its parent, the overall leaf is harder and more rigid and crisp; however, the growth rate and growth habit closely resemble those of its parent. The new variety has not borne fruit.

The juvenile leaves of the new variety tend to be slightly smaller than the parent, but the mature foliage maintains a deeper green coloration than the parent and has a more exaggerated acuminate leaf tip.

The new variety has been asexually reproduced vegetatively by rooted cuttings in Aalsmeer, The Netherlands. Asexual reproduction through succeeding generations has established that the combination of characteristics as herein disclosed for the new cultivar is firmly fixed and is retained through successive generations of asexual reproduction.

BRIEF DESCRIPTION OF THE ILLUSTRATION

The accompanying illustration shows a specimen of the new cultivar in a photo illustration as true to color as is reasonably possible to make in an illustration of this character.

DESCRIPTION OF THE NEW VARIETY

'Monique' has not been observed under all possible environmental conditions. The phenotypic expression may vary with variations in environment such as temperature, light intensity and day length. The following observations and descriptions are of plants grown in Aalsmeer, The Netherlands, in a greenhouse during the month of January. In this description, color references Royal Horticultural Society Colour Chart (RHSCC). The terminology used in the color descriptions herein refers to plate numbers in this color chart.

Classification:

*Botanical.*—*Ficus benjamina* cv. 'Monique'.

Parentage: Mutation of *Ficus benjamina* Exotica.

Propagation: By vegetative cuttings and other known asexual reproduction techniques.

PLANT

A. Form: Upright, multiple-branching woody ornamental.

B. Growth: Extremely vigorous with uniform branching.

*Height attained.*—0.25 to 6.0 meters.

C. Foliage:

1. *Size.*—About 70×150 mm, medium large, Code 5–7.
2. *Quantity.*—Multiple, numerous.
3. *Color.*—New foliage: Upper side — near 144A to near 143A. As indicated previously, a small dark green spot, near 137A, has been observed on juvenile leaves under low light conditions. The major portion of the leaf, however, is near 144A to 143A. As the leaf matures, the entire leaf darkens to near 137A. Old foliage: Upper side — near 137A
4. *Shape.*—Ovate-acuminate leaf tip.
5. *Texture.*—Smooth and glabrous.
6. *Veination.*—An insignificant feature approximately 1 mm or less.
7. *Form.*—Undulate-crenate.
8. *Margin.*—Crenate.
9. *Stipules.*—Leaves are glabrous.
10. *Auricle.*—Absent.
11. *Resistance to disease.*—Resistant to Anthracnose, *Agrobacterium radiobacter* tumefaciens, *Heterodera fici, Tarsonemus pallidus* and Pseudoccus.
12. *Variegation.*—None.

D. Wood:

*New shoots.*—Color — greenish-brown

*Old wood.*—Color — brown

GENERAL

Temperature range: To 0° C.

Internode spacing: About 27 to 30 mm.

Preferred growing conditions: 20° C. to 32° C.

Growth habit: Vigorous upright woody, multiple branching.

Leaves per stem: Multiple alternate.

I claim:

1. A new and distinct cultivar of *Ficus benjamina* named 'Monique', as illustrated and described, particularly characterized by a plant with ovate leaves which are undulate-crenate in form.

* * * * *

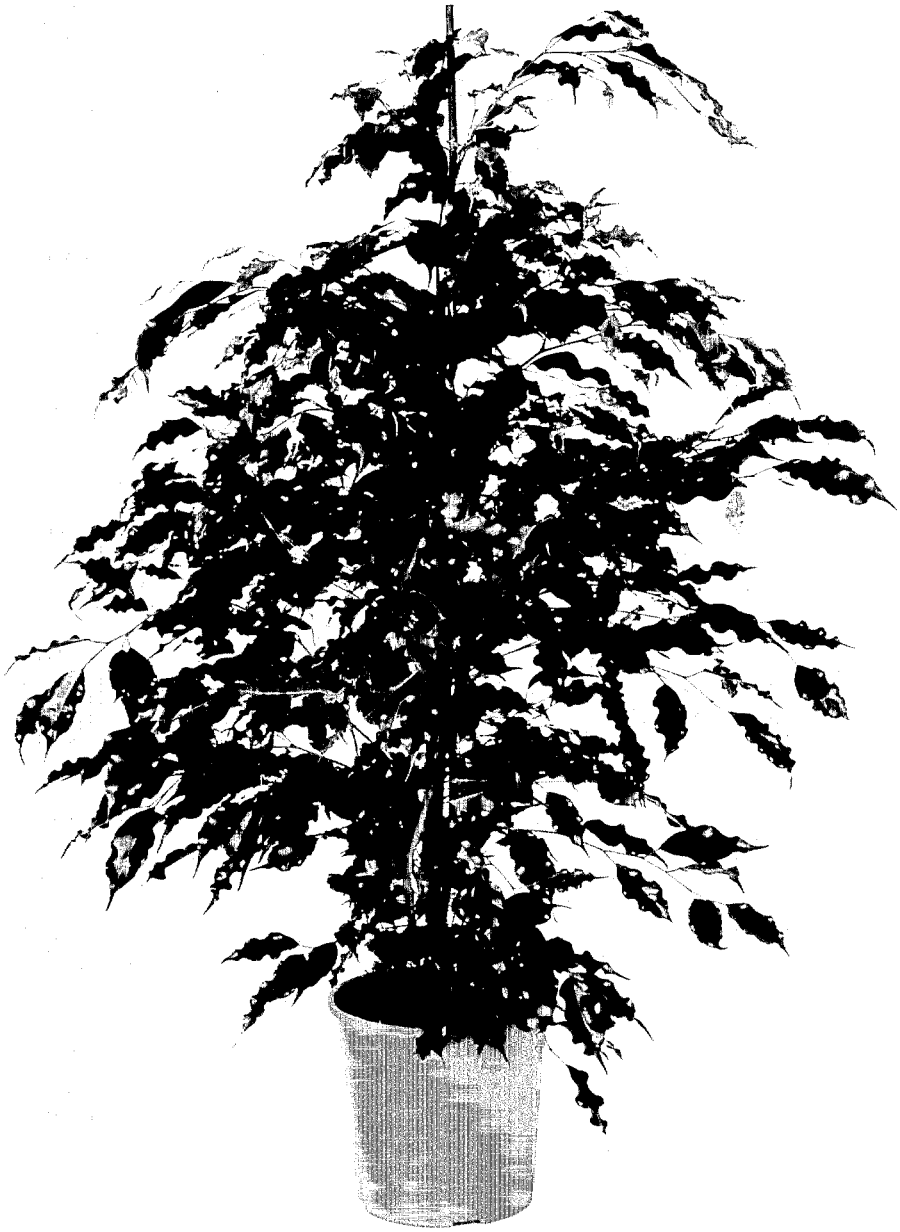

UNITED STATES PATENT AND TRADEMARK OFFICE

CERTIFICATE OF CORRECTION

PATENT NO. : Plant 8,637

DATED : March 8, 1994

INVENTOR(S) : Hubertus T. van Diemen

It is certified that error appears in the above-indentified patent and that said Letters Patent is hereby corrected as shown below:

Column 2, line 4, after "references" insert
-- are in accordance with the --.

Signed and Sealed this

Eighteenth Day of October, 1994

*Attest:*

*Attesting Officer*

BRUCE LEHMAN

*Commissioner of Patents and Trademarks*